United States Patent [19]
Lévesque et al.

[11] Patent Number: 6,057,927
[45] Date of Patent: May 2, 2000

[54] LASER-ULTRASOUND SPECTROSCOPY APPARATUS AND METHOD WITH DETECTION OF SHEAR RESONANCES FOR MEASURING ANISOTROPY, THICKNESS, AND OTHER PROPERTIES

[75] Inventors: Daniel Lévesque, Terrebonne; André Moreau, St-Bruno-de-Montarville; Marc Dubois; Jean-Pierre Monchalin, both of Montréal; Jean Bussière, St-Bruno; Martin Lord, Beloeil; Christian Padioleau, Montréal, all of Canada

[73] Assignee: American Iron and Steel Institute, Washington, D.C.

[21] Appl. No.: 09/030,400

[22] Filed: Feb. 25, 1998

[51] Int. Cl.$^7$ ................................................. G01B 9/02
[52] U.S. Cl. ..................... 356/432 T; 356/349; 356/357
[58] Field of Search ............................. 356/432 T, 432, 356/352, 357; 73/655, 657

[56] References Cited

U.S. PATENT DOCUMENTS

| | | | |
|---|---|---|---|
| 3,978,713 | 9/1976 | Penney | 73/67.7 |
| 4,581,939 | 4/1986 | Takahashi | 73/643 |
| 4,659,224 | 4/1987 | Monchalin | 356/352 |
| 4,710,030 | 12/1987 | Tauc et al. | 356/432 |
| 4,790,188 | 12/1988 | Bussiere et al. | 73/597 |
| 4,862,384 | 8/1989 | Bujard | 364/509 |
| 4,899,589 | 2/1990 | Thompson et al. | 73/597 |
| 4,905,519 | 3/1990 | Makowski | 73/657 |
| 4,966,459 | 10/1990 | Monchalin | 356/358 |
| 5,035,144 | 7/1991 | Aussel | 73/602 |
| 5,042,302 | 8/1991 | Soelkner | 73/597 |
| 5,080,491 | 1/1992 | Monchalin et al. | 356/352 |
| 5,226,730 | 7/1993 | Berthold | 374/119 |
| 5,251,486 | 10/1993 | Thompson et al. | 73/597 |
| 5,257,544 | 11/1993 | Khuri-Yakub et al. | 73/579 |
| 5,333,495 | 8/1994 | Yamaguchi et al. | 73/105 |
| 5,381,695 | 1/1995 | Payne et al. | 73/643 |
| 5,402,233 | 3/1995 | Schultz et al. | 356/351 |
| 5,457,997 | 10/1995 | Naruo et al. | 73/643 |
| 5,467,655 | 11/1995 | Hyoguchi et al. | 73/579 |
| 5,604,592 | 2/1997 | Kotidis et al. | 356/357 |
| 5,608,166 | 3/1997 | Monchalin et al. | 73/657 |

FOREIGN PATENT DOCUMENTS

| | | |
|---|---|---|
| 2172106 | 9/1986 | United Kingdom . |
| WO 93/24830 | 12/1993 | WIPO . |

OTHER PUBLICATIONS

Huang, et al., "Laser–based ultrasonics for flaw detection", *1994 IEEE Ultrasonics Symposium Proceedings*, vol. 2, (1994), pp. 1205–1209 (Abstract Only).

Huang, et al., "Laser–generation of narrow–band surface waves", *IEEE 1991 Ultrasonics Symposium Proceedings*, vol. 1 (1991), pp. 537–541 (Abstract Only).

Jia, et al., "Laser generated flexural acoustic waves travelling along the tip of a wedge", *IEEE 1993 Ultrasonics Symposium Proceedings*, vol. 2 (1993), pp. 637–640 (Abstract Only).

(List continued on next page.)

*Primary Examiner*—Robert H. Kim
*Assistant Examiner*—Andrew H. Lee
*Attorney, Agent, or Firm*—Fitzpatrick, Cella, Harper & Scinto

[57] ABSTRACT

Apparatus and method for detecting shear resonances includes structure and steps for applying a radiation pulse from a pulsed source of radiation to an object to generate elastic waves therein, optically detecting the elastic waves generated in the object, and analyzing the elastic waves optically detected in the object. These shear resonances, alone or in combination with other information, may be used in the present invention to improve thickness measurement accuracy and to determine geometrical, microstructural, and physical properties of the object. At least one shear resonance in the object is detected with the elastic waves optically detected in the object. Preferably, laser-ultrasound spectroscopy is utilized to detect the shear resonances.

45 Claims, 11 Drawing Sheets

OTHER PUBLICATIONS

Kawashima, "Nondestructive Characterization of Texture and Plastic Strain Ration of Metal Sheets with Electromagnetic Acoustic Transducers", *J. Acoust. Soc. Am.*, vol. 87, No. 2 (Feb. 1990), pp. 681–690.

Kawashima, et al., "On–Line Measurement of Plastic Strain Ratio of Steel Sheet Using Resonance Mode EMAT", *Journal of Nondestructive Evaluation*, vol. 12, No. 1 (1993), pp. 71–77.

Monchalin, "Progress Towards the Application of Laser–Ultrasonics in Industry", *Review of Progress in Quantitative Nondestructive Evaluation*, vol.12 (1993), pp. 495–506.

Monchalin, et al., "Laser–Ultrasonics: From the Laboratory to the Shop Floor", *Physics in Canada* (Mar./Apr. 1995), pp. 122–130.

Noroy, et al., "Shear–wave focusing with a laser–ultrasound phased–array", *IEEE Transactions on Ultrasonics, Ferroelectrics and Frequency Control*, vol. 42, No. 6 (Nov. 1995), pp. 981–988 (Abstract Only).

Ogi, et al., "Ultrasonic attenuation and grain–size evaluation using electromagnetic acoustic resonance," *J. Acoust. Soc. of Am.*, vol. 98, No. 1, Jul. 1995, pp. 458–464.

Schindel, et al., "High temperature pulsed photoacoustic studies of solids", *IEEE 1990 Ultrasonics Symposium Proceedings*, vol. 2 (1990), pp. 645–648 (Abstract Only).

Thompson, et al., "Angular dependence of ultrasonic wave propagation in a stressed orthorhombic continuum: Theory and application to the measurement of stress and texture", *J. Acoust. Soc. Am.*, vol. 80, No. 3 (Sep. 1996), pp. 921–931.

Wagner, "Breaking the sensitivity barrier: The challenge for laser–ultrasonics", *IEEE 1992 Ultrasonics Symposium Proceedings*, vol. 2 (1992), pp. 791–800 (Abstract Only).

Jean–Pierre Monchalin, et al., "Wall Thickness Measurement of Tubes and Eccentricity Determination by Laser–Ultrasonics", $39^{th}$ Mechanical Working & Steel Processing Conference, Iron & Steel Society, Indianapolis, IN, Oct. 19–22, 1997, Iron & Steel Society, Warrendale, PA.

Murayama, et al., "Development of an On–line Evaluation System of Formability in Cold–rolled Steel Sheets Using Electromagnetic Acoustic Transducers (EMATs)", *NDT&E International*, vol. 29 (1996), pp. 141–146.

Bunge, "Texture Analysis in Materials Science", Butterworth & co. (1982), pp. ix–xx, 1–119.

Roe, "Inversion of Pole Figures for Materials Having Cubic Crystal Symmetry", *J. Appl. Phys.*, vol.37 (1966), pp. 2069–2072.

Nuttal, "Some Windows With Very Good Sidelobe Behavior", *IEEE Trans on Acoust., Speech and Signal Processing*, vol. ASSP–29 (1981), pp. 84–91.

Sayers, "Angular Dependent Ultrasonic Wave Velocities in Aggregates of Hexagonal Crystals", *Ultrasonics*, vol.24 (1986), pp. 289–291.

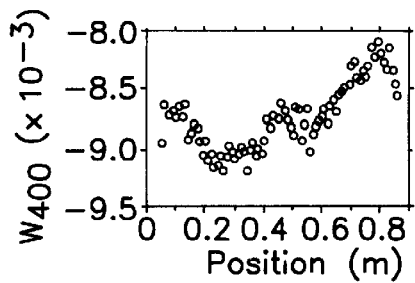
FIG. 14
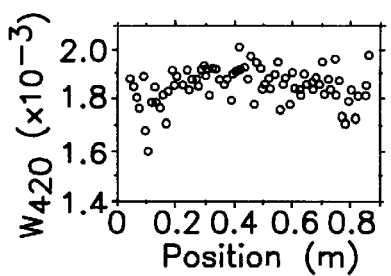
FIG. 15
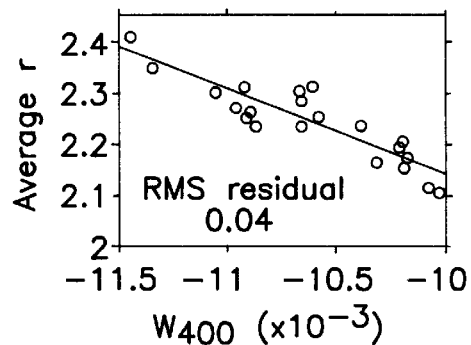
FIG. 16
FIG. 17
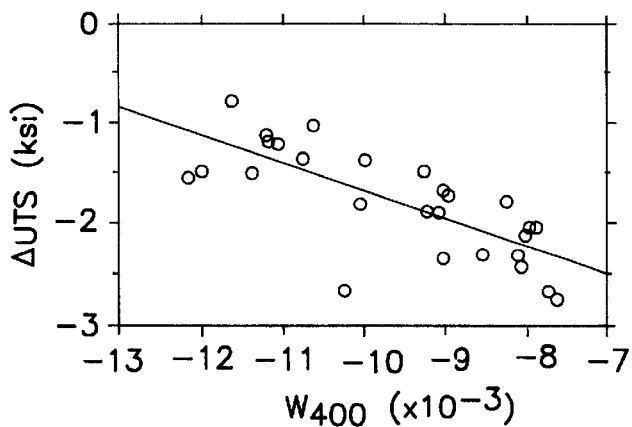
FIG. 18
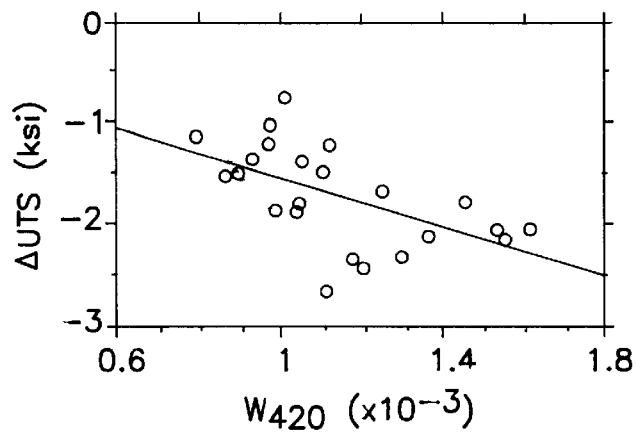

LASER-ULTRASOUND SPECTROSCOPY APPARATUS AND METHOD WITH DETECTION OF SHEAR RESONANCES FOR MEASURING ANISOTROPY, THICKNESS, AND OTHER PROPERTIES

STATEMENT OF GOVERNMENT RIGHTS

This invention was made with Government support under Contract No. DE-FC07-93ID13205 awarded by the Department of Energy. The Government has certain rights in this invention.

BACKGROUND OF THE INVENTION

1. Field of the Invention

The present invention relates to a spectroscopy apparatus and method, and preferably to a laser-ultrasound spectroscopy apparatus and method for detecting, measuring, or identifying one or more shear resonances in an object, and for calculating physical properties of the object, including, for example, thickness, anisotropy, and texture (i.e., the crystallographic orientation distribution), in accordance with the detected shear resonances.

2. Description of the Related Art

Ultrasonics generally refers to the principle of generating ultrasonic vibrations in an object, and then detecting the vibrations to determine the geometrical, microstructural, and physical properties of the object. This technique is advantageous because it is nondestructive.

Conventional ultrasound devices have been developed for detecting geometrical, microstructural, and physical properties of objects. One conventional ultrasound approach involves the use of transducers, including piezoelectric and electromagnetic acoustic transducers (EMATs). Examples include those discussed in U.S. Pat. No. 4,790,188 (Bussiére, et al.), U.S. Pat. Nos. 4,899,589 (Thompson, et al.) and 5,251,486 (Thompson, et al.), and Thompson, et al., "Angular Dependence of Ultrasonic Wave Propagation in a Stressed Orthorhombic Continuum: Theory and Application to the Measurement of Stress and Texture", *J. Acoust. Soc. Am.*, Vol. 80, No. 3 (September 1996), pp. 921–931. In these conventional approaches, texture (i.e., the crystallographic orientation distribution) or other properties are evaluated by measuring angular variations of elastic wave velocities or plate mode velocities. However, a number of drawbacks exist. First, these conventional approaches require sending and receiving ultrasound in various directions in the plane of a plate, for example, at 0, 45, and 90 degrees to the rolling direction. Secondly, the piezoelectric approach requires immersion or water coupling, or contact with the object being tested, while the EMAT approach, although non-contact, requires the sensor to be very close to the sheet surface, e.g., 1 mm, and these requirements could cause problems if the object or metal sheet is hot, lifts off when moving, or presents irregularities such as welds between two pieces. Thirdly, conventional ultrasonic devices are often subject to precise orientation requirements, with angular tolerance being a few degrees or less, meaning that the inspection of curved surfaces requires a surface contour following device.

Another conventional approach is the electromagnetic acoustic resonance (EMAR) technique, as exemplified by (a) U.S. Pat. No. 5,467,655 (Hyoguchi, et al.); (b) Kawashima, "Nondestructive Characterization of Texture and Plastic Strain Ratio of Metal Sheets with Electromagnetic Acoustic Transducers", *J. Acoust. Soc. Am.*, Vol. 87, No. 2 (February 1990), pp. 681–690; and (c) Kawashima, et al., "On-Line Measurement of Plastic Strain Ratio of Steel Sheet Using Resonance Mode EMAT", *Journal of Nondestructive Evaluation*, Vol. 12, No. 1 (1993), pp. 71–77. The EMAR technique generally involves exciting the EMAT by RF (radio frequency) narrow-band tonebursts while sequentially sweeping through a frequency range of interest. However, drawbacks exist in that this approach requires an EMAT, which suffers from the problems described above, and in that this approach requires multiple measurements to cover a wide frequency bandwidth.

Another ultrasound technique is laser-ultrasonics, wherein one laser is used to generate ultrasonic vibrations in an object, and another is used for detection. Either laser may be coupled through an optical fiber for ease of handling. Examples of this approach include those discussed in U.S. Pat. Nos. 4,659,224 (Monchalin) and 4,966,459 (Monchalin). This approach is advantageous because it does not require either the generation laser or the laser-interferometer detector to be close to the sheet. Furthermore, unlike an EMAT or piezoelectric transducer, the generation laser and laser-interferometer are not subject to precise orientation requirements, because their operation is substantially orientation insensitive. Conventional laser-ultrasound devices have been used, for example, to measure time of flight between two longitudinal echoes, and from that measurement to determine thickness (e.g., Jean-Pierre Monchalin, et al., "Wall Thickness Measurement of Tubes and Eccentricity Determination by Laser-Ultrasonics", 39th Mechanical Working & Steel Processing Conference, Iron & Steel Society, Indianapolis, Ind., Oct. 19–22, 1997, Iron & Steel Society, Warrendale, Pa.).

However, we have found that conventional ultrasound devices have not been able to determine thickness corrected for texture. Thickness corrected for texture (also referred to as independent of texture) is an ultrasonic measurement of thickness which takes into account the crystallographic orientation distribution of the object. Texture here refers to the crystallographic orientation distribution of polycrystalline aggregates. Because the ultrasonic velocity in a single crystal depends on the direction of propagation within the single crystal, the ultrasonic velocity in a polycrystalline aggregate depends on the average orientation of the crystallites with respect to the propagation direction of the ultrasound. Variations of the crystallographic orientation distribution (texture variations) commonly found in metals can cause variations of the ultrasonic velocity in excess of 1%, thus limiting thickness measurement accuracy using time of flight measurements to 1% at best.

Texture measurements are also useful measurements in determining a large number of physical properties, such as ductility and formability (the ability to plastically deform), and the anisotropy of physical properties such as tensile strength, which are of great importance to manufacturing industries (as discussed in Murayama, et al., "Development of an On-line Evaluation System of Formability in Cold-rolled Steel Sheets Using Electromagnetic Acoustic Transducers (EMATs)", *NDT&E International*, Vol. 29 (1996), pp. 141–146; and Bunge, "Texture Analysis in Materials Science", Butterworth & Co. (1982)).

We have found that to improve thickness measurement accuracy or to make some texture measurements with ultrasonics, it is necessary to measure shear acoustic wave velocities, and one way to measure these velocities is to search for resonances in an object. However, we have found that laser-ultrasound devices have not been able to detect and measure shear resonances in an object.

Accordingly, we have found that a need exists for an improved laser-ultrasound device which can detect geometrical, physical, and microstructural properties of an object even more accurately, and which can detect and measure shear resonances in an object.

SUMMARY OF THE INVENTION

In view of the foregoing, it is a principal object of the present invention to provide an improved ultrasound apparatus and method, and preferably an improved laser-ultrasound apparatus and method.

Another object of the present invention is to provide a laser-ultrasound apparatus and method (also referred to as a laser-ultrasound spectroscopy apparatus and method) which can detect and measure at least one shear resonance in an object, and preferably which can detect and measure at least one longitudinal resonance and one shear resonance in an object, and most preferably, which can detect and measure longitudinal and shear resonances in the thickness of an object, i.e., associated with elastic or ultrasonic waves propagating in the thickness of the object. An ultrasonic resonance arises from the propagation of an ultrasonic vibration (also called an elastic wave) between the boundaries of an object in such a way that constructive interference arises at a particular location and at a particular frequency. For example, an ultrasonic resonance can arise in a plate when an ultrasonic vibration propagates in the thickness direction and when the ultrasonic vibration has a half wavelength equal to an integral multiple of the plate thickness. A longitudinal resonance refers to an ultrasonic resonance of a longitudinal wave, i.e., of an elastic wave polarized in the propagation direction. A shear resonance refers to an ultrasonic resonance of a shear wave, i.e., of an elastic wave polarized in a direction perpendicular to the propagation direction. FIG. 19 is an explanatory perspective view to further explain the concepts of direction of propagation and polarization of elastic waves in an object. In that figure, object 1000 is, by way of example and not of limitation, a rolled steel plate. The x axis indicates the rolling direction of the plate, the y axis represents the transverse (width) direction, and the z axis denotes the direction of the thickness of the plate. The thickness of the plate is designated by reference character e. The thick arrow shows the direction of propagation of elastic waves in the thickness of the plate or perpendicular to the surface of the plate, i.e., in the z direction. Such elastic waves may be (a) longitudinal waves, i.e., waves having a polarization in the direction of propagation (as denoted by thin arrow zz) or (b) shear waves, i.e., waves having a polarization perpendicular to the direction of propagation (as denoted, for example, by thin arrows zx (rolling direction) or zy (transverse direction)). Of course, the present invention is not limited to use with a plate, or of these polarizations.

Another object of the present invention is to provide a laser-ultrasound apparatus and method which can accurately measure properties of an object, including, by way of example and not of limitation, geometrical properties, physical properties, and microstructural properties of the object. Examples include thickness (a geometrical property), texture (i.e., crystallographic orientation distribution, which is a microstructural property), elastic constants (a physical property), and plastic strain ratio (a physical property).

In particular, for example, it is an object of the present invention to provide an apparatus and method for measuring both thickness and texture of an object, and preferably to use the texture measurement to improve thickness measurements. (In the present invention, this has resulted in thickness measurement accuracies of about 0.1%.)

Still another object of the present invention is to provide a laser-ultrasound apparatus and method which can detect and measure one or more shear ultrasonic shear resonances in the thickness of a plate.

Yet another object of the present invention is to provide an improved laser-ultrasound apparatus and method which can excite, and then detect and measure one or more ultrasonic shear resonances in the thickness of a plate, or one or more ultrasonic shear resonances and a longitudinal resonance in the thickness of a plate.

Still another object of the present invention is to provide an improved laser-ultrasound apparatus and method for measuring and detecting one or more shear resonances, and for determining physical properties of an object, including, for example, thickness, texture (crystallographic orientation distribution and crystallographic orientation distribution coefficients such as W400 and W420 in the representation of Roe (Roe, "Inversion of Pole Figures for Materials Having Cubic Crystal Symmetry", *J. Appl. Phys.*, Vol. 37 (1966), pp. 2069–2072; incorporated herein by reference) or similar coefficients in other representations (Bunge, "Texture analysis in materials science", Butterworth & Co (1982); incorporated herein by reference), formability, and anisotropy, in accordance with the detected shear resonances.

In view of the foregoing objects, in one aspect, the present invention relates generally to (a) using a pulsed source of radiation (e.g., a pulsed laser) to generate a broadband ultrasonic pulse in a plate, (b) using a laser interferometer to optically detect the ultrasonic signal that reverberates in the plate, (c) analyzing the detected signal to locate and measure the resonance frequencies of longitudinal and shear resonances, and (d) relating the measured ultrasonic resonance frequencies to the geometrical, microstructural, and physical properties of the material.

In another aspect, the present invention relates to an apparatus comprising generating means for applying a radiation pulse from a pulsed source of radiation to an object to generate elastic waves therein, detecting means for optically detecting the elastic waves generated in the object by the generating means, and analyzing means for analyzing the elastic waves optically detected in the object by the detecting means, the analyzing means comprising shear resonance identifying means for identifying at least one shear resonance in the object in accordance with the elastic waves optically detected in the object by the detecting means.

In yet another aspect, the present invention relates to an apparatus comprising generating means for applying a radiation pulse from a pulsed source of radiation to an object to generate elastic waves therein, detecting means for optically detecting the elastic waves generated in the object by the generating means, and analyzing means for analyzing the elastic waves optically detected in the object by the detecting means, the analyzing means comprising (a) shear resonance identifying means for identifying at least one shear resonance in the object in accordance with the elastic waves optically detected in the object by the detecting means, and (b) longitudinal resonance identifying means for identifying a longitudinal resonance in the object in accordance with the elastic waves optically detected in the object by the detecting means.

In still another aspect, the present invention relates to a laser-ultrasonic spectroscopy device, comprising a laser for directing a laser pulse to a object to generate elastic waves in the object, a laser-interferometer for detecting surface displacements in the object arising from the elastic waves generated by the laser pulse of the laser, a converter for converting the surface displacements detected by the laser-interferometer from the time domain to the frequency domain to obtain frequency domain data, or spectrum, a shear resonance detector for detecting and measuring at least one shear resonance in accordance with the frequency domain data, and a property calculator for calculating at least one of a physical, geometrical, and microstructural property of the object in accordance with the at least one shear resonance detected and measured by the shear resonance detector.

In still a further aspect, the present invention relates to a method for generating and optically detecting a shear resonance in an object, the method comprising applying a radiation pulse from a pulsed source of radiation to an object to generate elastic waves therein, optically detecting the elastic waves generated in the object by the applying step, and analyzing the elastic waves optically detected in the object by the detecting step, the analyzing steps comprising a shear resonance identifying step of identifying at least one shear resonance in the object in accordance with the elastic waves optically detected in the object by the detecting step.

In yet another aspect, the present invention relates to a method for generating and optically detecting a shear resonance and a longitudinal resonance in an object, the method comprising applying a radiation pulse from a pulsed source of radiation to an object to generate elastic waves therein, optically detecting the elastic waves generated in the object by the applying step, and analyzing the elastic waves optically detected in the object by the detecting step, the analyzing steps comprising (a) a shear resonance identifying step of identifying at least one shear resonance in the object in accordance with the elastic waves optically detected in the object by the detecting step and (b) a longitudinal resonance identifying step for identifying a longitudinal resonance in the object in accordance with the elastic waves optically detected in the object by the detecting step.

In yet another aspect, the present invention relates to a method comprising directing a laser pulse to an object to generate elastic waves in the object, optically detecting surface displacements in the object arising from the elastic waves generated by the laser pulse of the laser, converting the surface displacements detected by the detecting step from the time domain to the frequency domain to obtain frequency domain data, a shear resonance detecting step of detecting at least one shear resonance in accordance with the frequency domain data, and calculating properties of the object in accordance with the at least one shear resonance detected by the shear resonance detecting step.

In a still further aspect, the present invention relates to an apparatus including a pulsed source of radiation for applying a radiation pulse to an object to generate elastic waves therein, an interferometer for optically detecting surface displacements in the object arising from the elastic waves generated by the radiation pulse generated by said pulsed source of radiation, and a resonance detector for detecting, in accordance with the surface displacements detected by said interferometer, a resonance of elastic waves propagating in the direction of the thickness of the object and having a polarization along an axis perpendicular to the direction of propagation.

In still a further aspect, the present invention relates to a laser-ultrasound device for measuring at least one of thickness and texture of a sample by detecting at least one shear wave in the direction normal to the surface of the sample, or by detecting a longitudinal wave and at least one shear wave in the direction normal to the surface of the sample. This detection of the longitudinal and/or shear waves using the present invention includes, in addition to or as an alternative to detection of resonance (i.e., frequency domain), detection of the time delay between successive echoes (i.e., time of flight, or delay of propagation in the time domain).

These and other objects, aspects, advantages and features of the present invention will become more apparent from the following detailed description of the preferred embodiments taken in conjunction with the accompanying drawings.

BRIEF DESCRIPTION OF THE DRAWINGS

FIGS. 14 and 15 are graphs respectively showing measurement of $W_{400}$ and $W_{420}$ as a function of position across the width of a plate;

FIG. 16 is a graph showing a correlation between $W_{400}$ and r-bar;

FIG. 17 is a graph showing a correlation between $W_{400}$ and $\Delta$UTS (where UTS refers to ultimate tensile strength);

FIG. 18 is a graph showing a correlation between $W_{420}$ and $\Delta$UTS; and

DESCRIPTION OF THE PREFERRED EMBODIMENTS

Figure 1:
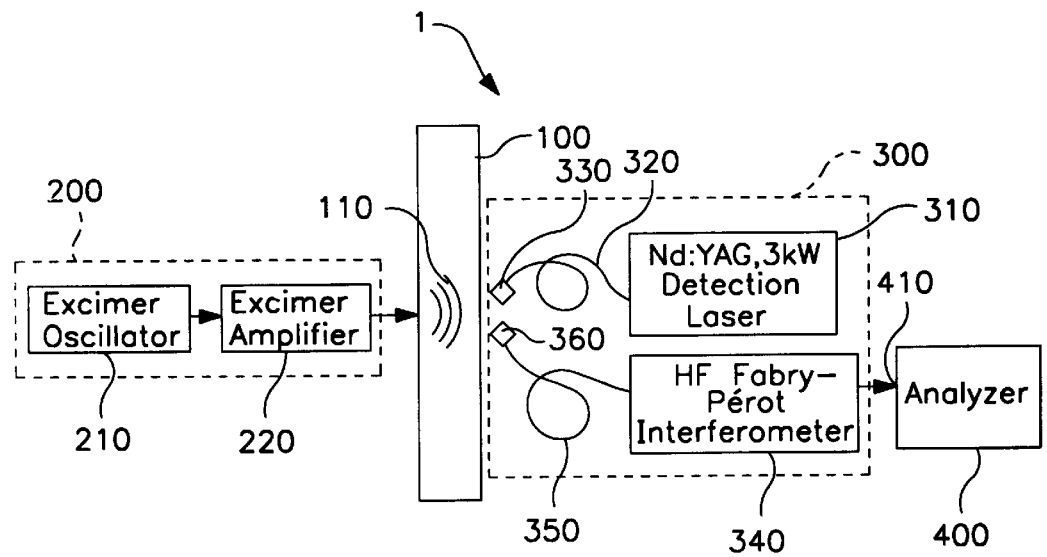
FIG. 1 is a schematic block diagram of a preferred embodiment in accordance with the present invention.

The preferred embodiment of a laser-ultrasound spectroscopy apparatus or device according to the present invention is schematically depicted in FIG. 1. Generally designated by reference numeral 1, the apparatus includes a pulsed generation laser 200, a laser interferometer 300, and an analyzer 400. Reference numeral 100 represents a sample object, e.g., a flat steel sheet or plate, being tested in the apparatus. Preferably, the sample object is a plate material (i.e., a material with two parallel surfaces that is much wider than thick). However, the present invention is not limited to such sample objects, and may be used to test objects of other shapes including, for example, cylinders, hollow cylinders (pipes), spheres, hollow spheres (shells), or any shape that can give rise to acoustic resonances.

In general terms, the apparatus operates as follows: the pulsed generation laser 200 directs a laser pulse onto the sheet 100. When the laser pulse hits the sheet 100, a broadband ultrasonic pulse is generated in the sheet. In other words, a single-shot laser pulse simultaneously excites or generates a broad frequency spectrum of elastic waves 110 (also called ultrasonic waves or vibrations) in the sheet. The elastic waves echo back and forth through the thickness of the sheet (e.g., from one surface to another), causing a small surface motion. This motion, and thus the elastic waves that reverberate in the thickness of the sheet, are detected by the laser interferometer 300. Finally, based on the detected elastic waves, the analyzer 400 identifies, isolates, detects, or measures not only longitudinal resonances, but also shear resonances. Having done so, the analyzer 400 then uses the detected shear and longitudinal resonances to calculate geometrical, microstructural, and physical properties of the sheet.

Now we will describe the individual components in more detail.

The Generation Laser

The generation laser 200 emits and directs a laser light pulse onto the surface of the sheet 100. Preferably, the generation laser 200 is a laser that can excite elastic waves of large amplitudes in the object. Depending on the application, this laser may be a $CO_2$ laser, a Nd:Yag laser, an excimer laser, or any other pulsed laser. The generation laser 200 can also be any continuous or long pulse laser followed by an optical switching device. In this preferred embodiment, an excimer laser is used to generate acoustic waves in metals because excimer lasers emit UV (ultraviolet) radiation which is more efficient than visible or infrared radiation wavelengths at generating ultrasonic waves in metals. More specifically, an excimer laser of the KrF type (radiation wavelength of 248 nm) with a pulse duration of 6 ns fwhm (i.e., full width at half maximum) and an energy of 200 mJ per pulse is preferably used as the generation laser 200. This laser was made by amplifying a 6 ns, 5 mJ pulse from a small excimer laser (excimer oscillator 210) by a larger excimer laser (excimer amplifier 220).

This laser was used for convenience and currently available commercial excimer lasers with pulse duration of 15 ns and pulse energy of 500 mJ or more are expected to perform at least as well.

It is preferred that the generation laser 200 be focused on an area selected so that the laser energy or power density is sufficiently large to keep the energy density at high enough levels (preferably more than 10 $MW/cm^2$ in metals) to generate large amplitude ultrasound vibrations in the sheet 100. For example, when the sheet 100 is a 1 mm thick steel sheet, it is preferred that the generation laser 200 be focused to an area having a dimension of about 6 mm×8 mm. This is because the dimension of the focused laser spot influences the amplitude of shear resonances excited by the laser pulse. Such resonances are small compared to the longitudinal resonances excited by the laser pulse. The above-described focusing arrangement was selected to aid in increasing the amplitude of the shear resonances.

When the generation laser 200 emits and directs a laser pulse onto the surface of the sheet 100, an ultrasonic pulse is generated in the sheet. To generate such a pulse, the generation laser 200 may be operated either in a thermoelastic regime or an ablative regime. In the former mode of operation, the laser pulse causes an ultrasonic pulse without removing material from the surface of the sheet. In the latter, which we prefer, the laser pulse causes a slight ablation (or removal) of material, mostly of dirt, oil, or other material present on the surface, resulting in a recoil which generates the ultrasonic pulse.

The ultrasonic pulse contains a broad frequency spectrum (between 0 Hz and 40 MHz or higher) of elastic waves in the sheet. Initially after the laser pulse, the elastic waves traveling in or near the direction perpendicular to the surface are mostly longitudinal waves. After several roundtrips in the thickness of the sheet, some of the longitudinal wave energy is mode-converted to shear wave energy. This arises as a result of the small angles of incidence to the surface of the longitudinal waves or vibrations. For sheets of cubic metals, two distinct shear modes, slow mode (referred to as Ss or Sslow) and fast mode (referred to as Sf or Sfast), both having polarization parallel to the surface (i.e., perpendicular to the direction of propagation of the longitudinal elastic waves), develop and propagate in the thickness with slightly different velocities.

Figure 2:
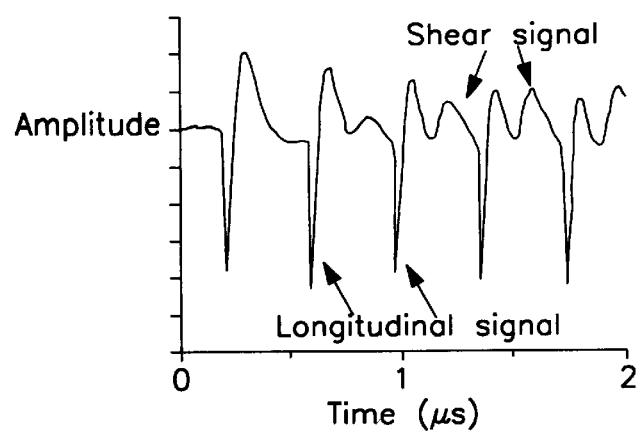
FIG. 2 is a graph showing a time signal comprising the first few ultrasonic echoes through the thickness of a plate.
Figure 3:
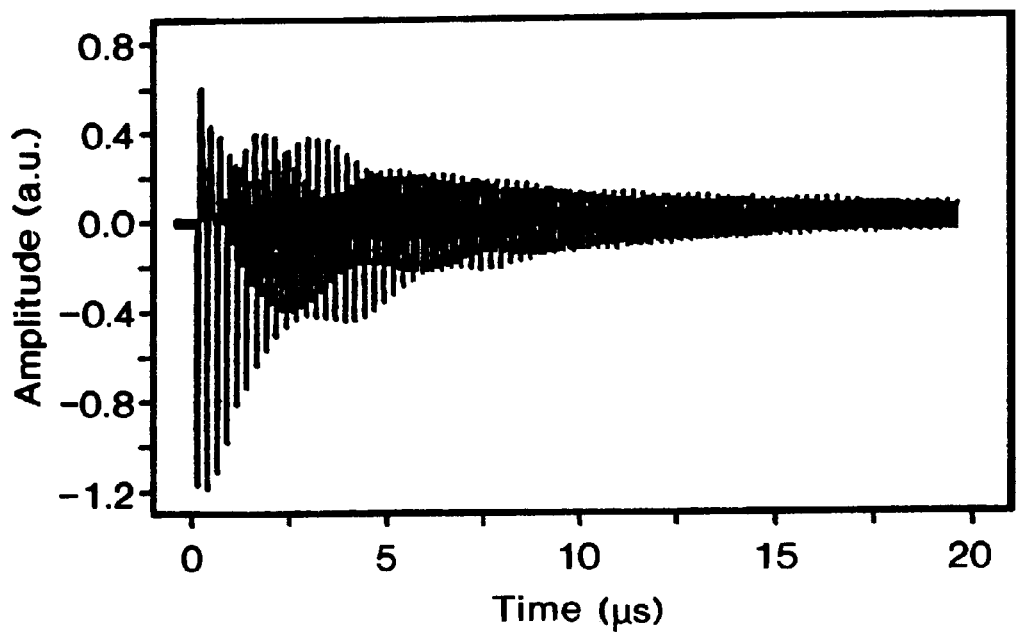
FIG. 3 is a graph showing a time signal comprising hundreds of ultrasonic echoes through the thickness of a plate.

FIGS. 2 and 3 are graphs illustrating the above-discussed longitudinal and shear elastic waves, and in particular the surface displacement of the sheet caused by these waves. In each figure, the x-axis represents time (in $\mu s$) and the y-axis represents the amplitude of surface displacement of the sheet, in arbitrary units. FIG. 2 shows a time signal (i.e., a signal in the time domain) including the first several vibrations or echoes. FIG. 3 shows a time signal comprising hundreds of vibrations or echoes.

The Laser Interferometer

The surface displacements caused by the elastic waves are detected by the laser interferometer 300, which outputs a signal representative of the amplitude of surface displacements as a function of time (referred to as the time signal or time domain signal).

The main components of the laser interferometer 300 are (a) a detection laser 310, preferably a pulsed detection laser, and more preferably a long pulse Nd:YAG 3 kW laser (manufactured by Ultraoptec), and (b) an interferometer 340, preferably a confocal Fabry-Perot interferometer (manufactured by UltraOptec) because this type of interferometer has a large light gathering capability and because it is insensitive to speckles. However, other interferometers may be used, such as a Michelson, Mach-Zender, photorefractive, photo-emf, or any other type of interferometer with a detection bandwidth that includes the frequencies of the resonance peaks of interest, and with good signal to noise characteristics (state-of-the-art interferometers are currently limited by shot noise). In the preferred embodiment, the laser interferometer 300 further includes the following conventional components: an optical fiber 320, illumination optics 330 and collection optics 360, and an optical fiber 350. Pulsed laser light emitted by the detection laser 310 passes through the optical fiber 320 to illumination optics 330, which direct the laser pulse to the surface of the sheet 100. There, the laser pulse is scattered and reflected by the surface of the object and is modulated (in phase or frequency) by the surface displacements caused by the elastic waves, and is collected by the collection optics 360 to pass through the optical fiber 350 to the interferometer 340, which includes an unshown photodetector for detecting the light. By using the optical fibers, the detection laser 310 and interferometer 340 may be located at a distance from the sheet 100. This may be especially advantageous if the sheet 100 is a hot steel sheet moving on a production line, or the like.

It is preferred that a maximum number of photons be collected on the photodetector of the interferometer 340, so as to improve the signal to noise ratio. To effect this goal, an InGaAs photodiode is used as a photodetector inside the interferometer because it has high quantum efficiency and because it can handle several hundred mW of light without saturating. The illumination optics 330 preferably includes a conventional arrangement of any combination of one or several lenses capable to focus the detection laser light onto a 4 mm wide area on the surface of the sheet. The collection optics 360 preferably includes a conventional arrangement of any combination of lenses capable of imaging the 4 mm wide area that is illuminated onto the optical fiber 350.

The Analyzer

Figure 5:
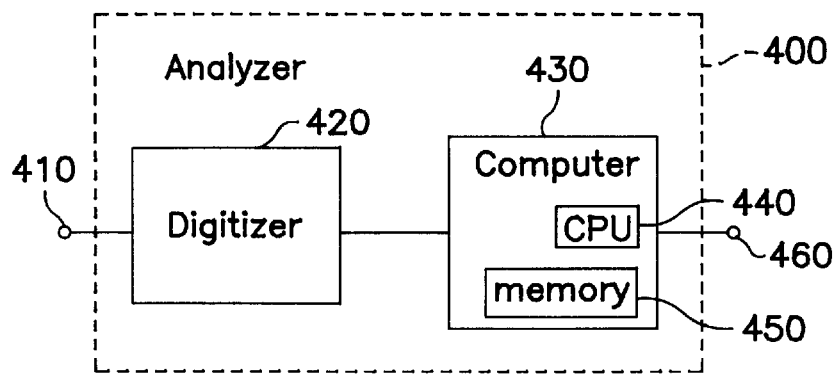
FIG. 5 is a schematic block diagram illustrating a preferred analyzer circuit according to the present invention.

The time signal output by the interferometer 340 is received at an input 410 by the analyzer 400. The analyzer 400 then processes this signal to detect shear and longitudinal resonances, and calculates geometrical, microstructural, and physical properties such as thickness and texture as a function of the detected resonances. As schematically depicted in FIG. 5, the analyzer 400 includes (a) a digitizer or digital sampling device 420, which receives and digitizes the time signal input from the interferometer 340 via input 410, and (b) a personal computer 430 for receiving the digitized data from the digitizer 420 and for processing the data.

Turning first to the digitizer 420, it is preferred to digitize the time signal with a resolution in excess of 8 bits. This may be accomplished, for example, by using a 10-bit or 12-bit digitizer, or alternatively by using an 8-bit digitizer used with oversampling and/or with signal averaging to increase the number of significant bits to more than 8. In the preferred embodiment, the digitizer 420 includes an 8-bit digitizer (manufactured by Lecroy, model number 9384) operating at 1 Gsample/s (i.e., 1 gigasample per second) to digitize resonances in the 2 MHz to 15 MHz bandwidth, and at least 20 measurements are averaged together.

The digitized data is then output by the digitizer 420 to the personal computer 430 for processing. The processing of the digitized data is effected by the CPU (central processing unit) 440 of the computer 430. The CPU 440 then executes a control program stored in the memory 450 to analyze the digitized data.

Figure 6A:
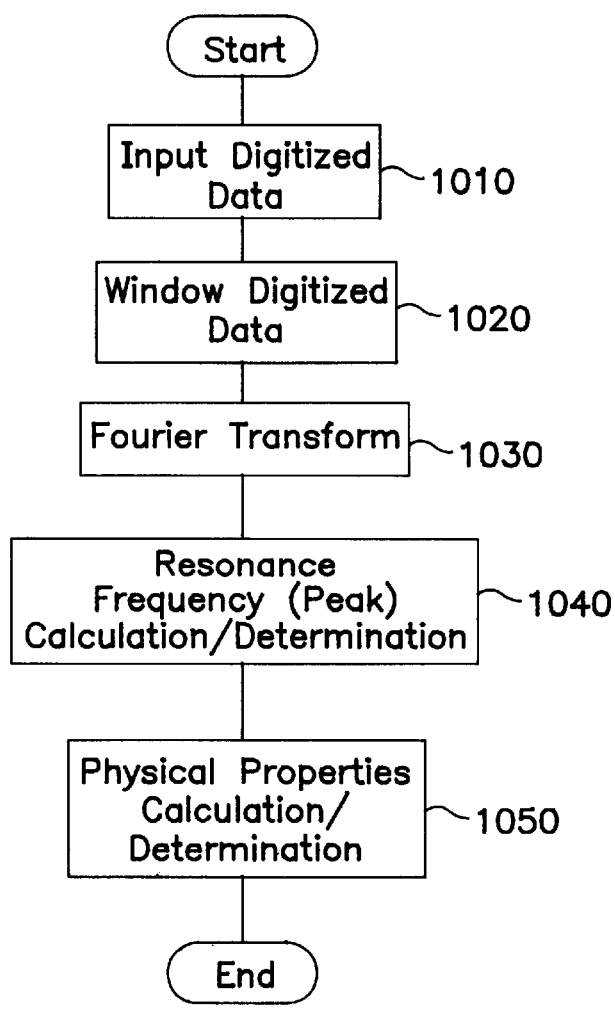
FIG. 6A is a flowchart illustrating the steps of a procedure for resonance analysis in accordance with the present invention.

The main, preferred steps of the control program are shown in FIG. 6A and include: (1) a step of inputting the digitized data from the digitizer 420 to the computer 430, and storing the same in memory 450 (step 1010); (2) a step of windowing the digitized data (step 1020); (3) a step of converting the windowed digitized data from the time domain (i.e., amplitude of surface displacement versus time) to the frequency domain (i.e., amplitude of surface displacement versus frequency; also referred to as the frequency domain representation or spectrum), preferably by using a discrete Fourier transform (step 1030); (4) a step of identifying, detecting, and measuring resonances in the frequency domain (step 1040); and (5) a step of calculating physical properties (such as thickness, texture, and the like) in accordance with the detected resonances (step 1050).

In more detail, in step 1010, the digitized data is input by the computer 430 from the digitizer 420, and is stored in the memory 450. The above-discussed FIGS. 2 and 3 depict this digitized time signal data.

In step 1020, the digitized data input in step 1010 is windowed. Preferably, for a 1 mm thick steel sheet, the first 20 $\mu$s of the digitized time domain data is windowed. It is preferred that the window used is an optimal Blackman window, such as Blackman-Harris window (Nuttall, "Some Windows With Very Good Sidelobe Behavior", *IEEE Trans on Acoust., Speech and Signal Processing*, Vol. ASSP-29 (1981), pp. 84–91). The purpose of windowing the data is to minimize leakage while keeping good frequency resolution. Such a window improves the ability to detect faint shear resonances, or to resolve two resonances with slightly differing resonant frequencies in the discrete Fourier transform step 1030.

Having been windowed, the windowed digitized data is converted from the time domain to the frequency domain in step 1030, preferably by a discrete Fourier transform. When the signal is analyzed in the frequency domain using the present invention, separate resonances may be observed, including those for the two shear waves (Sfast and Sslow) when a large number of echoes are analyzed together.

Figure 4:
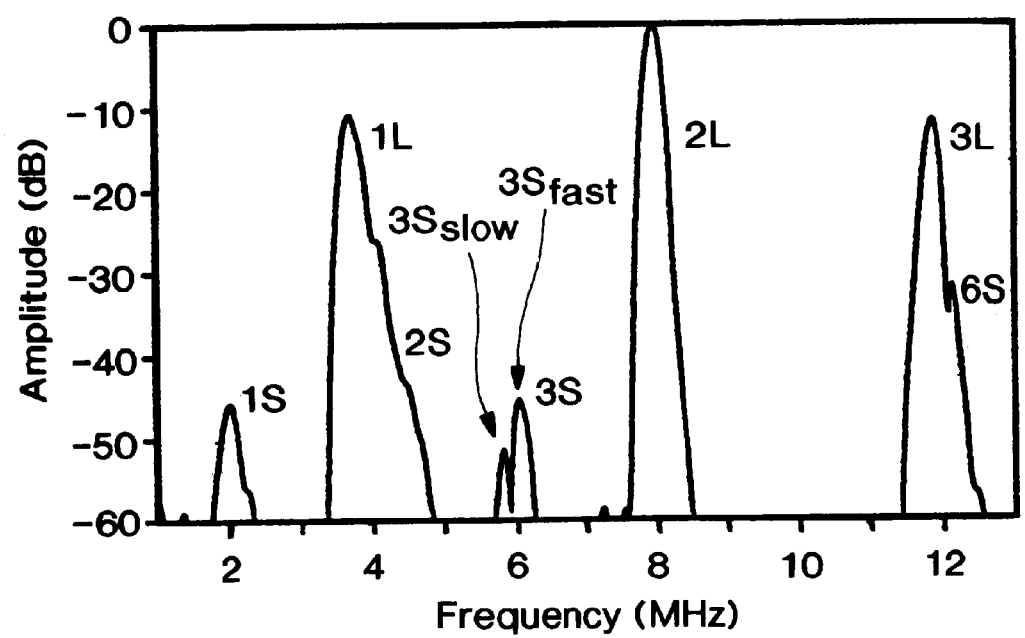
FIG. 4 is a graph showing longitudinal and shear resonances in the frequency domain.

FIG. 4 is a frequency domain graph showing the results of the discrete Fourier transform of the time signal of FIG. 3. In FIG. 4, the y-axis represents amplitude in dB, while the x-axis represents frequency in MHz. The peaks labeled 1L, 2L, and 3L are longitudinal resonances, and respectively represent the first, second, and third order harmonics of the longitudinal mode of vibration. The peaks labeled 1S, 2S, 3S, and 6S are shear resonances, and respectively represent the first, second, third, and sixth order harmonics of shear modes of vibration. For the third harmonic shear resonance, 3S, the individual shear resonances or resonance peaks for the slow and fast shear modes discussed above were easily distinguishable, and are designated by 3Sslow (slow shear mode) and 3Sfast (fast shear mode). In examining the Fourier transformed data, it was found that the signal amplitudes for the shear resonances were much smaller than those of the longitudinal resonances. For example, as shown in FIG. 4, the signal amplitudes for the 3S shear resonances were smaller than those of the L resonances by about 40 dB. Accordingly, it is preferred that the apparatus have a signal to noise ratio at least of order 200, preferably at least of order 500, so that the shear resonances may be observed. The preferred embodiment achieves a dynamic range of 70 dB between the highest peak amplitude and the noise floor in the frequency domain, corresponding to a signal to noise ratio of about 3000.

Figure 11:
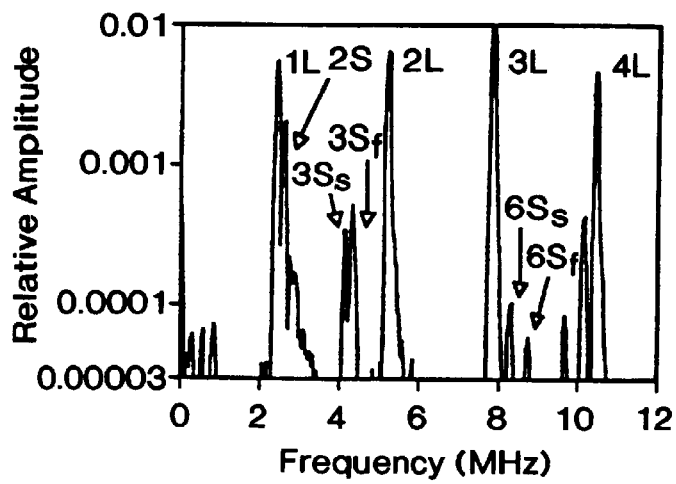
FIG. 11 is a graph showing longitudinal and shear resonances in the frequency domain.

FIG. 11 is another example of a frequency domain graph showing the results of a discrete Fourier transform of a time signal in accordance with the present invention. In that figure, not only are the 3Sslow (3Ss) and 3Sfast (3Sf) resonances easily distinguishable, so also are the 6Sslow (6Ss) and 6Sfast (6Sf) resonances.

The digitized data having been converted to the frequency domain in step 1030 (FIG. 6A), in step 1040, resonances (or resonance peaks) in the frequency domain are identified, detected, and measured. In the preferred embodiment, we identify one longitudinal resonance and two shear resonances (Sslow and Sfast), and calculate their respective resonance frequencies, which we shall refer to as $F_L$, $f_{Sslow}$, and $f_{Sfast}$. We prefer to use the 2L longitudinal resonance and the 3Sslow and 3Sfast shear resonances. This is because, as can be seen from FIG. 4, these resonance peaks are separate and distinct in comparison with the other longitudinal and shear resonances. Of course, the present invention is not limited to these specifics, and any one or more resonances may be employed.

Figure 6B:
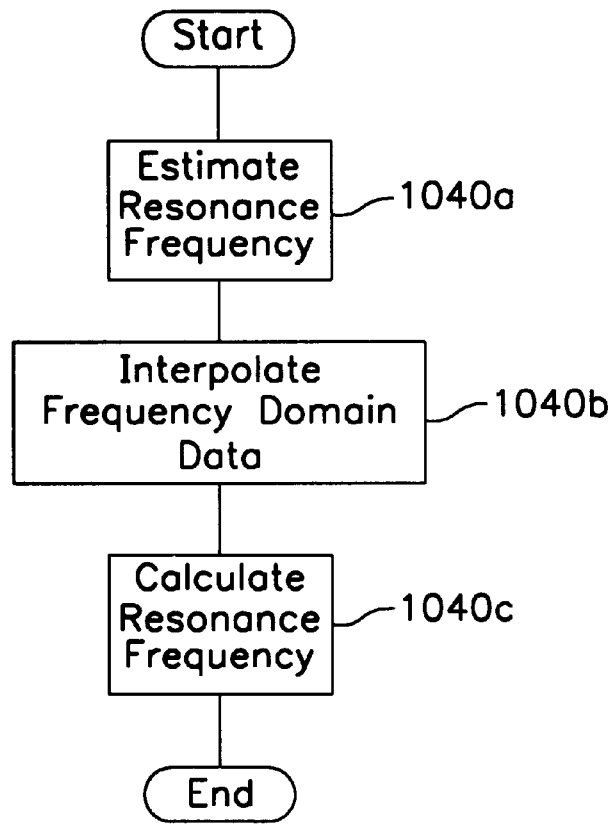
FIG. 6B is a flowchart illustrating the steps of a procedure for calculating the resonance frequency of a resonance in accordance with the present invention.

To identify, detect, and measure the resonances in step 1030, the following exemplary procedure preferably is employed, as shown in FIG. 6B: (1) first, resonance frequencies of selected resonances are estimated (Step 1040a), (2) next, the frequency domain data is interpolated around the estimated resonance frequencies by using a cubic spline (Step 1040b), and (3) then, from the interpolated data, the resonance frequency at the maximum amplitude of the resonance peak is calculated (Step 1040c).

To estimate the resonance frequencies of the selected resonances (Step 1040a), we prefer to estimate the resonance frequency of the fundamental (first order) resonance of that mode of vibration, and then to multiply that value by the order of the resonance. For example, to estimate the resonance frequencies of the 2L, 3Sslow, and 3Sfast resonances in FIG. 4, we estimate the resonance frequencies of the fundamental longitudinal, Sslow, and Sfast resonances, and then multiply by 2 or 3 as the case may be. When estimating the resonance frequencies of the fundamental resonances, we prefer to use one of the following three methods:

(1) One way to estimate the resonance frequency of a fundamental longitudinal or shear resonance is to use a priori knowledge of the approximate longitudinal or shear wave velocity for a plate made of a given material and of the thickness of the plate. For example, the estimated resonance frequency of the fundamental resonance may be obtained by dividing the velocity by twice the thickness, in other words, f=v/2 h.

(2) Another way to estimate a resonance frequency of a fundamental resonance is to measure the time delay between two successive echoes of the longitudinal elastic wave. The estimated resonance frequency of the fundamental longitudinal resonance is very close to the inverse of this time delay. The estimated resonance frequency of a fundamental shear resonance can then be determined on the basis of a priori knowledge of the ratio of shear wave velocity to longitudinal wave velocity for a plate made of a given material. For example, the estimated resonance frequency of a fundamental shear resonance can be found by multiplying the frequency of the fundamental longitudinal resonance by the ratio of the shear to longitudinal wave velocity. In steel, for example, that ratio is about 6000/3300.

(3) A third way to estimate the resonance frequencies of fundamental resonances is to determine the smallest frequencies whose integral multiples correspond to the observed resonance frequencies of plural detected resonances, i.e., a common divisor operation. There can be from one to three such frequencies corresponding to the longitudinal and two shear fundamental resonance frequencies.

Once the frequency of a fundamental longitudinal or shear resonance is estimated, that value is then multiplied by the order of the resonance to obtain an estimated frequency of that resonance. For example, the estimated 2L frequency is obtained by doubling the estimated resonance frequency of the fundamental longitudinal resonance, while the estimated 3Sslow resonance frequency is obtained by tripling the estimated frequency of the fundamental slow shear resonance.

Once resonance frequencies of selected resonances have been estimated, then, as discussed above, the resonances are quantitatively identified by interpolating the frequency domain data around the estimated resonance frequency (Step 1040b), and from the interpolated data, calculating the resonance frequency by determining the frequency at the maximum amplitude of the resonance peak (Step 1040c).

Figure 6C:
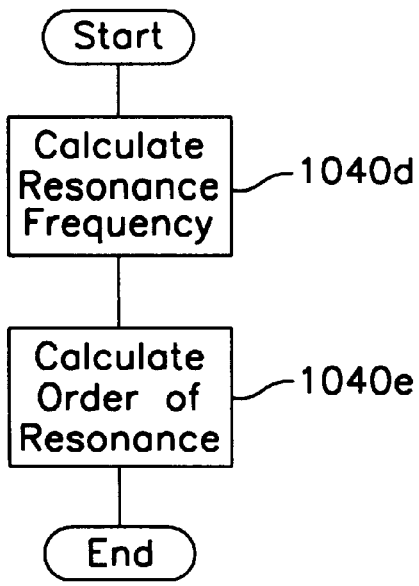
FIG. 6C is a flowchart illustrating the steps of a procedure of calculating the order of a resonance in accordance with the present invention.

The foregoing procedure is given by way of example and not of limitation. Any other method for identifying resonances in the frequency domain may be used. If the order of a given resonance is unknown, then a procedure such as that in FIG. 6C may be used to calculate the order. In step 1040d, the resonance frequency of a given resonance is calculated. In step 1040e, the order of that resonance is calculated by, for example, dividing the resonance frequency by an estimated resonance frequency of a fundamental resonance and taking the nearest integer.

In step 1050 of FIG. 6A, physical properties are determined as a function of the resonances identified in step 1040. In the preferred embodiment, the physical properties are determined as a function of the resonance frequencies and associated orders of one longitudinal resonance (2L) and two shear resonances (3Sslow and 3Sfast). These physical properties may include, for example, thickness, and, in the case of polycrystalline aggregates, a measurement of the crystallographic orientation distribution (COD) of the polycrystalline aggregate (which distribution may be either isotropic or anisotropic). Measurements of COD are also known as measurements of texture, and are effected by obtaining measurements of crystallographic orientation distribution coefficients (CODCs) including $W_{400}$ and $W_{420}$ in the representation of Roe (Roe, "Inversion of Pole Figures for Materials Having Cubic Crystal Symmetry", *J. Appl. Phys.*, Vol. 37 (1966), pp. 2069–2072; incorporated herein by reference). The former coefficient is a measure of crystallographic alignment in the direction normal to the plane of the sheet, and the latter is a measure of two-fold anisotropy in the plane of the sheet.

For example, in the preferred embodiment, the object is a plate of weakly anisotropic material, wherein weakly anisotropic is defined in terms of the macroscopic elastic constants $C_{ij}$ as:

$$C_{ij} = C°_{ij} + \Delta C_{ij}$$

with $$|\Delta C_{ij}| \ll C°_{ij}$$

where $C°_{ij}$ is any one of the isotropic, texture-free components and $|\Delta C_{ij}|$ is a perturbation to the isotropic approximation (Sayers, "Angular Dependent Ultrasonic Wave Velocities in Aggregates of Hexagonal Crystals", *Ultrasonics*, Vol. 24 (1986), pp. 289–291; incorporated herein by reference). Moreover, if the plate is a polycrystalline aggregate of cubic crystallites having a macroscopic orthotropic symmetry, then the following equations may be used:

$$e = \sqrt{\frac{\lambda + 4\mu}{4\rho(f_L^2/n_L^2 + f_{Sfast}^2/n_{Sfast}^2 + f_{Sslow}^2/n_{Sslow}^2)}} \quad \text{Equation (1)}$$

$$W_{420} = \frac{56\sqrt{5}\,\rho e^2(f_{Sslow}^2/n_{Sslow}^2 - f_{Sfast}^2/n_{Sfast}^2)}{64\pi^2 A} \quad \text{Equation (2)}$$

$$W_{400} = \frac{35\sqrt{2}\,(4\rho e^2 f_L^2/n_L^2 - (\lambda + 2\mu))}{64\pi^2 A} \qquad \text{Equation (3)}$$

Here, e is the thickness of the plate, $f_L$ is the resonance frequency of a longitudinal resonance, $n_L$ is the order of the longitudinal resonance, $f_{Sslow}$ is the resonance frequency of a slow shear resonance, $n_{Sslow}$ is the order of the slow shear resonance, $f_{Sfast}$ is the resonance frequency of a fast shear resonance, $n_{Sfast}$ is the order of the fast shear resonance, $\rho$ is the mass density of the plate, $\lambda$ and $\mu$ are the Lamé elastic constants of the plate in the isotropic approximation, and A is the anisotropic factor of the cubic crystallites, defined as $A = c_{11} - c_{12} - 2c_{44}$, where $c_{ij}$ are the single-crystal elastic constants.

In these equations, it is understood that if the resonance frequencies of the fast and slow shear resonances with $n_{Sslow}$ and $n_{Sfast}$ are so close to each other that the two resonances cannot be separated, then $f_{Sslow}$ and $f_{Sfast}$ are equal.

Accordingly, the present invention provides a measurement of thickness which is independent of (i.e., corrected for) texture, as well as measurement of two CODCs: $W_{400}$ and $W_{420}$. These values may in turn be used to measure a variety of other geometrical, physical, and microstructural properties. For example, $W_{440}$ may be estimated because $W_{400}$ and $W_{420}$ often correlate with $W_{440}$ due to material processing. Also, the elastic constants $C_{33}$, $C_{44}$ and $C_{55}$ may be obtained, in the usual system of coordinates whereby the z axis is normal to the plane, using the following equations:

$$C_{33} = 4\rho e_2(f_L^2/n_L^2)$$

$$C_{44} = 4\rho e_2(f_{Sfast}/n^2_{Sfast})$$

$$C_{55} = 4\rho e_2(f^2_{Sslow}/n^2_{Sslow})$$

Furthermore, using the above texture coefficients ($W_{400}$, $W_{420}$ and $W_{440}$), one may use the procedure described by Kawashima (Kawashima, "Nondestructive Characterization of Texture and Plastic Strain Ratio of Metal Sheets with Electromagnetic Acoustic Transducers", *J. Acoust. Soc. Am.*, Vol. 87 (1990), pp. 681–690; incorporated herein by reference) to calculate all nine macroscopic elastic constants of polycrystalline aggregates of cubic materials. Measurement of plastic strain ratio (r) average plastic strain ratio (r-bar) and variations of plastic strain ratio, including $\Delta r$, may also be obtained. These parameters are defined as:

r-bar = $[r(0°) + 2r(45°) + r(90°)]/4$ $\Delta r = [r(0°) - 2r(45°) + r(90°)]/2$ where $r(\theta)$ is the plastic strain ratio at an angle $\theta$ with respect to a reference direction, such as the rolling direction. For example, the parameter r-bar may be estimated from known relationships with $W_{400}$ (Murayama, et al., "Development of an On-line Evaluation System of Formability in Cold-rolled Steel Sheets using Electromagnetic Acoustic Transducers (EMATs)", *NDT&E International*, Vol. 29 (1996), pp. 141–146; incorporated herein by reference).

More generally, if any linear or non-linear relationship may be established between any one or several of the resonant frequencies detected by the sensor, or any one or several of the derived quantities such as thickness, $W_{400}$, $W_{420}$, the elastic constants, and any microstructural or physical property of the material, then the present apparatus may be used to measure this microstructural or physical property. In this regard, FIG. 16 is a graph showing a correlation between $W_{400}$ (x-axis) and r-bar (y-axis) in an ultra-low carbon (ULC) steel sheet. In this fashion, we measured r-bar with an accuracy of +/−0.04 (root mean square of the residual between the data and the linear least squares fit). In like fashion, the present invention may be used to measure the anisotropy of tensile properties of materials, such as ultimate tensile strength, because the anisotropy of the tensile properties of materials depends on texture. FIGS. 17 and 18 are graphs showing correlations between $W_{400}$ (FIG. 17 x-axis) or $W_{420}$ (FIG. 18 x-axis) and the four-fold, in-plane variations of the ultimate tensile strength, $\Delta$UTS. This parameter is defined as:

$\Delta$UTS = [UTS(0°) − 2UTS(45°) + UTS(90°)]/2 where UTS($\theta$) is the ultimate tensile strength at an angle $\theta$ with respect to a reference direction, such as the rolling direction. Therefore, these correlations may be used as a calibration to provide a measurement of r-bar and $\Delta$UTS based on the sensor's measurements of $W_{400}$ and $W_{420}$. In these examples, and in any others, the calibration relies on establishing a relationship between a specific property and any of the sensor's quantities. In particular, these relationships may be obtained using a linear or non-linear curve fitting technique to the data. Accordingly, in addition to measurements of e (thickness), $W_{400}$, and $W_{420}$, and the elastic constants $C_{33}$, $C_{44}$ and $C_{55}$, the present invention may be used to calculate a variety of physical and microstructural parameters including, but not limited to: w440, yield strength (YS), tensile strength (TS), total elongation (TE), uniform elongation (UE), strain hardening exponent (n), the plastic strain ratio parameters r-bar and $\Delta r$, and the like.

EXAMPLES

As an example of the foregoing, the apparatus according to FIG. 1 was used to test a steel plate formed of ultra low carbon steel (ULC) (manufactured by LTV Steel, 0.776 mm thickness). The results were as follows: $f_L$=7.959 MHz, $n_L$=2, $f_{Sslow}$=5.818 MHz, $n_{Sslow}$=3, $f_{Sfast}$=6.042 MHZ, $n_{Sfast}$=3, e=0.772 mm, $W_{400}$=−10.01×10⁻³, and $W_{420}$=+1.99×10⁻³.

Comparative Test Results

Test results indicate that the present invention provides improved and accurate measurements of physical properties, including thickness and texture.

Figure 7A:
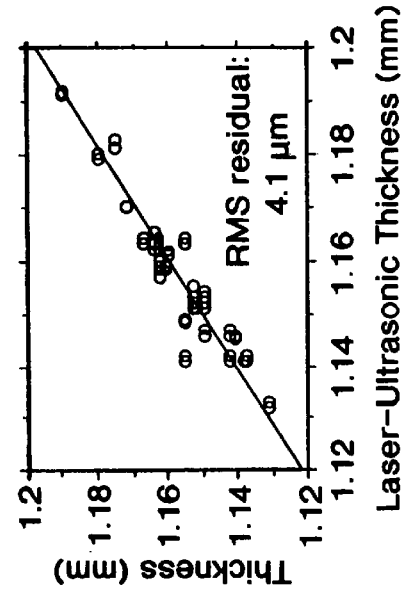
FIGS. 7A through 7C are graphs showing thickness measurements in accordance with the present invention versus thickness measurements taken by a micrometer.
Figure 7B:
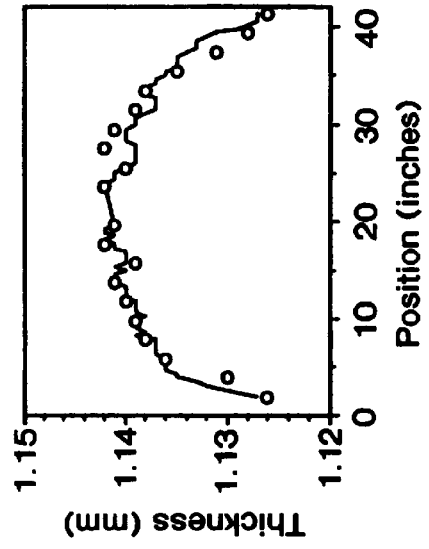
Figure 7C:
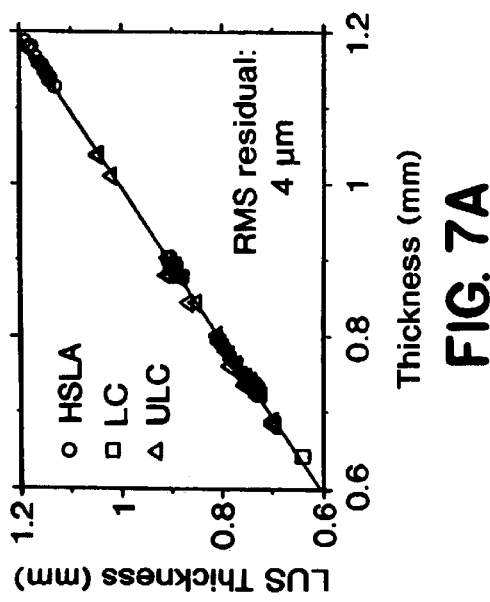

In one test using the apparatus of FIG. 1, the thickness of three different steels, ultra low carbon steel (ULC) (manufactured by LTV Steel, grade 9355 and 9356, dimensions 1'×1' approximately), low carbon steel (LC) (manufactured by Weirton Steel, grade 1005, dimensions 1'×1' approximately), and high strength low alloy steel (HSLA) (manufactured by LTV Steel, grade 050XF, dimensions 1'×1' approximately) (each of the three steels having different textures), was measured using the present invention and using a micrometer. FIG. 7A is a graph showing the results of the test, with the x-axis being the micrometer measurement and the y-axis being the laser-ultrasonics measurement (LUS) according to the present invention. For about 100 samples total, the thickness measurement precision (root mean square residual to the correlation) was 4 $\mu$m, demonstrating excellent accuracy, even across three steel grades with very different chemistries, textures, and microstructures. FIGS. 7B and 7C are graphs showing results of a test for HSLA sheets, with the y-axis being the micrometer measurement (using a micrometer with flat tips in FIG. 7B and using a micrometer with rounded tips in FIG. 7C) and the x-axis being the LUS measurement according to the present invention. The rms (root mean square) residuals were 4.1 and 1.6 $\mu$m, respectively, demonstrating that the ultrasound spectroscopy according to the present invention is more accurate than the measurement made with the micrometer with flat tips. In fact, it was determined that laser-ultrasound spectroscopy thickness measurement repeatability on a single location on a sheet is better than 1 $\mu$m, i.e., better than the repeatability achieved with the micrometer with rounded tips.

Figure 8:
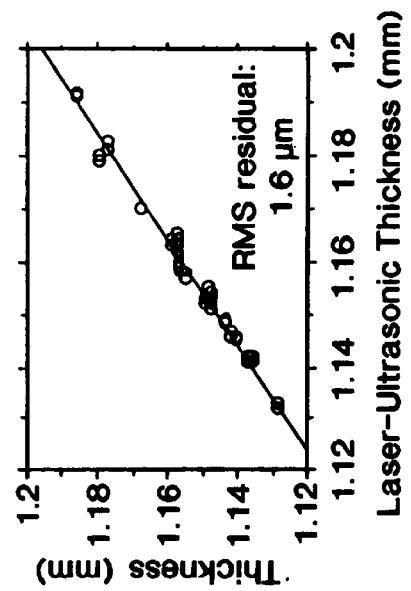
FIG. 8 is a graph showing thickness measurements taken across the width (i.e, transverse direction) of a plate.

In another test, thickness variations on a single sheet of HSLA steel were measured, as shown in FIG. 8, which is a graph wherein the x-axis indicates the position across the width (transverse direction) of a steel sheet, and the y-axis represents the thickness, the solid line represents the laser-ultrasonics thickness measurement according to the present invention, while the circles represent micrometer measurements. Here, the measurement precision was found to be of order 1 $\mu$m or better, with most of the difference between the laser-ultrasound measurement and the micrometer measurement being attributed to the micrometer measurement, thereby demonstrating excellent accuracy.

Figure 12:
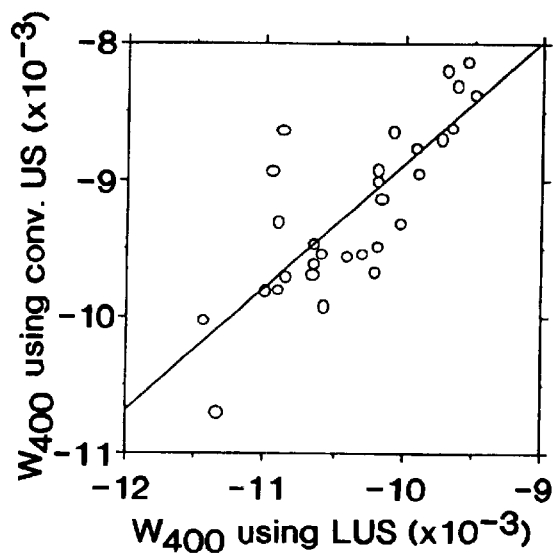
FIG. 12 is a graph showing $W_{400}$ measurements in accordance with the present invention versus $W_{400}$ measurements taken using conventional, non-laser ultrasonics.
Figure 13:
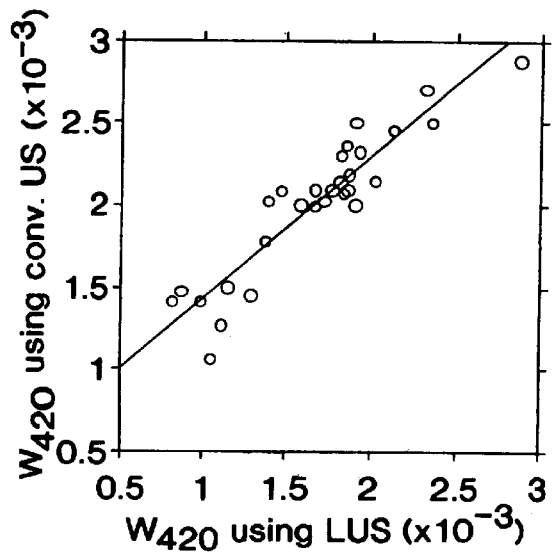
FIG. 13 is a graph showing $W_{420}$ measurements in accordance with the present invention versus $W_{420}$ measurements taken using conventional, non-laser ultrasonics.
Figure 19:
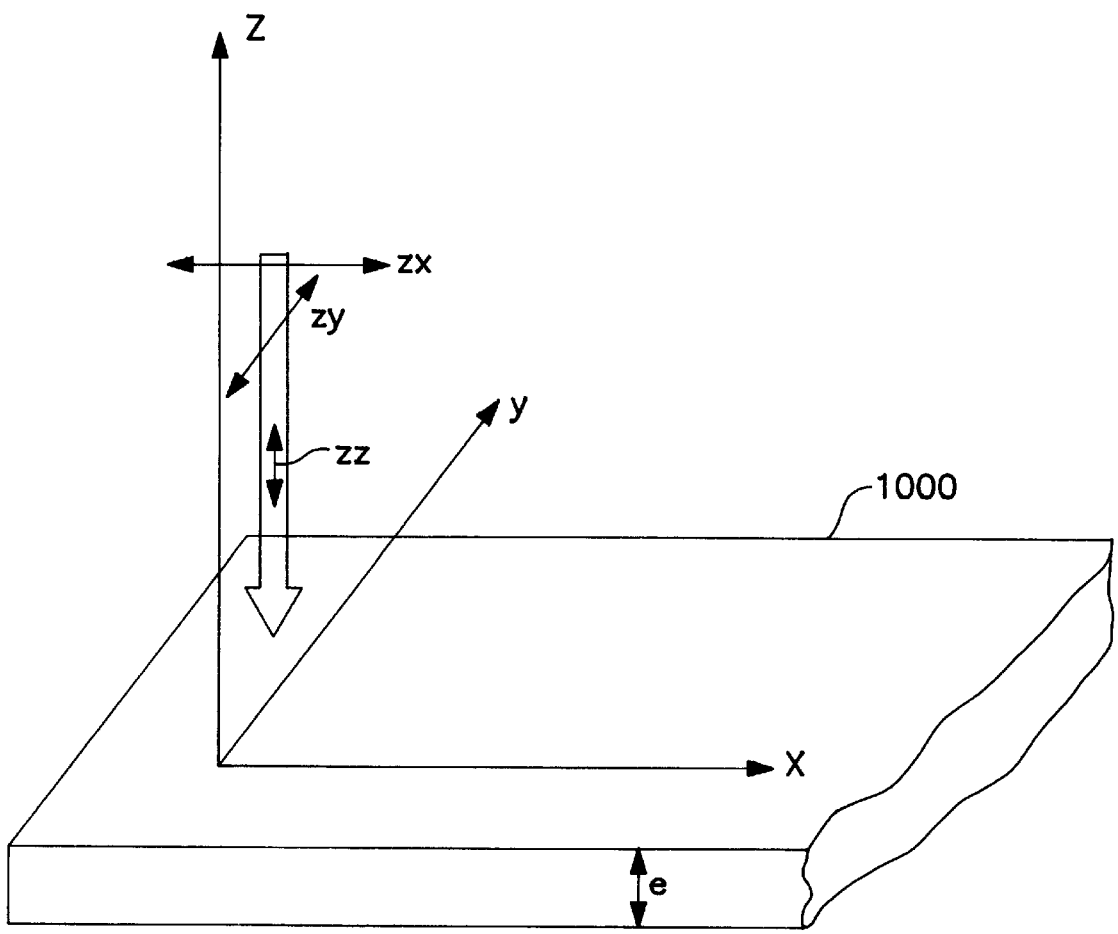
FIG. 19 is an explanatory perspective view showing the propagation direction and polarization of elastic waves in an object.

In another test, $W_{400}$ and $W_{420}$ were measured both using conventional, non-laser ultrasound (piezoelectric transducers) and using the present invention. The results are respectively shown in FIGS. 12 and 13. Each figure shows the conventional ultrasound approach results on the y-axis, with results calculated using the present invention on the x-axis. As can be seen, there is good agreement between the conventional ultrasound approach results and those achieved using the present invention.

In yet another test, the present invention was used to calculate $W_{400}$ and $W_{420}$ as a function of position across the width of a steel sheet. FIGS. 14 and 15 respectively show $W_{400}$ and $W_{420}$ (y-axis) as a function of position across the width of a steel sheet (x-axis). Overall, the present invention afforded a thickness measurement accuracy on the order of 0.1%, or 1 $\mu$m, i.e., better than a micrometer, and also afforded accurate measurements of $W_{400}$, $W_{420}$, and other parameters estimated therefrom.

Alternate Embodiments

Figure 9:
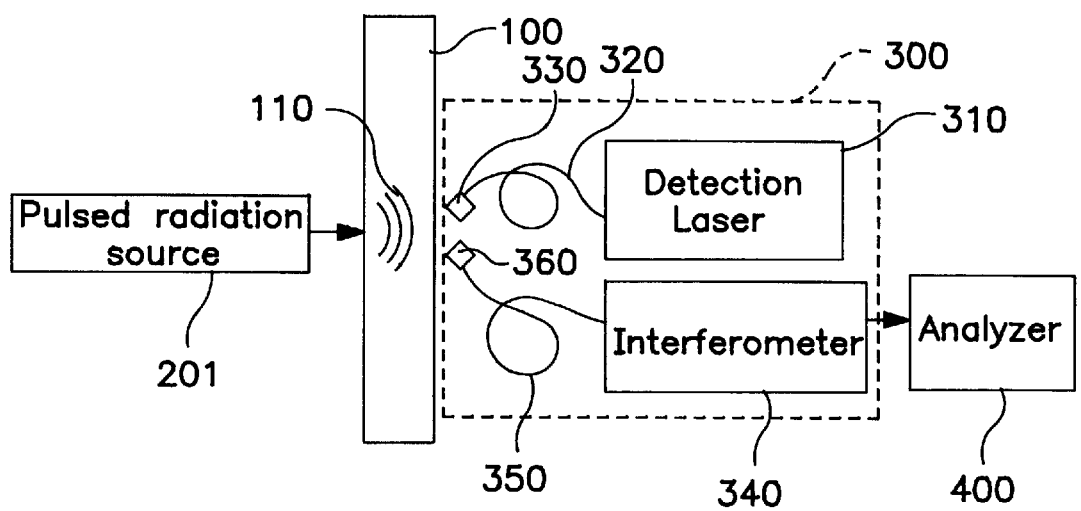
FIG. 9 is a schematic block diagram illustrating an alternate embodiment of the present invention.

Although the preferred embodiment has been described as using a pulsed generation laser 200, the present invention is not limited thereto, and may instead employ a radiation source for applying radiation to the object, preferably a pulsed radiation source for applying a radiation pulse to the object. Examples include synchrotron radiation, strobed light, discharge tube (e.g., flash lamp), and pulsed electron beams. FIG. 9 depicts an alternate embodiment of the present invention, wherein the same reference numerals depict the same components, and wherein the pulsed generation laser has been replaced by a pulsed radiation source 201. This pulsed radiation source 201 is also shown in another alternate embodiment shown in FIG. 10A, wherein the optical fibers and illumination and collection optics of the laser interferometer of the preferred embodiment are replaced with optics 315 for illuminating and collecting light.

Figure 10A:
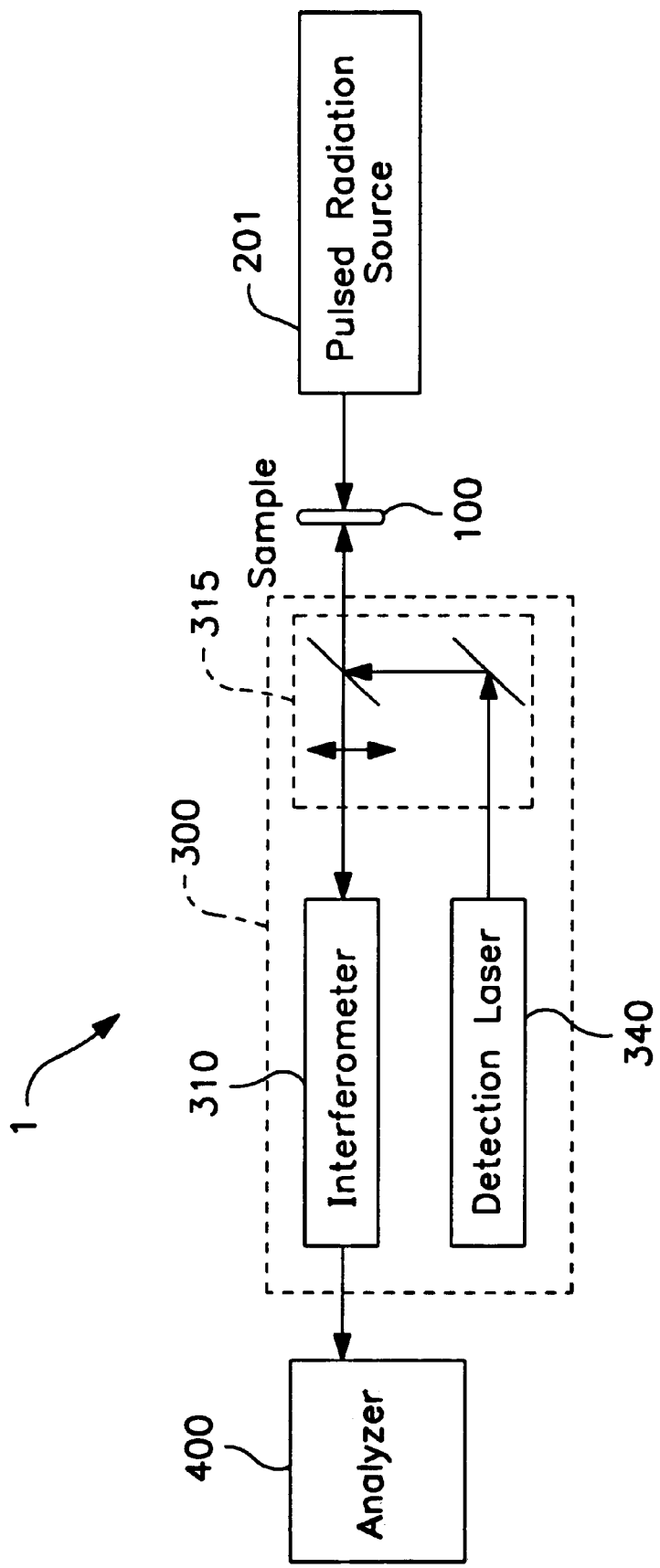
FIG. 10A is a schematic block diagram illustrating yet another alternate embodiment of the present invention.
Figure 10B:
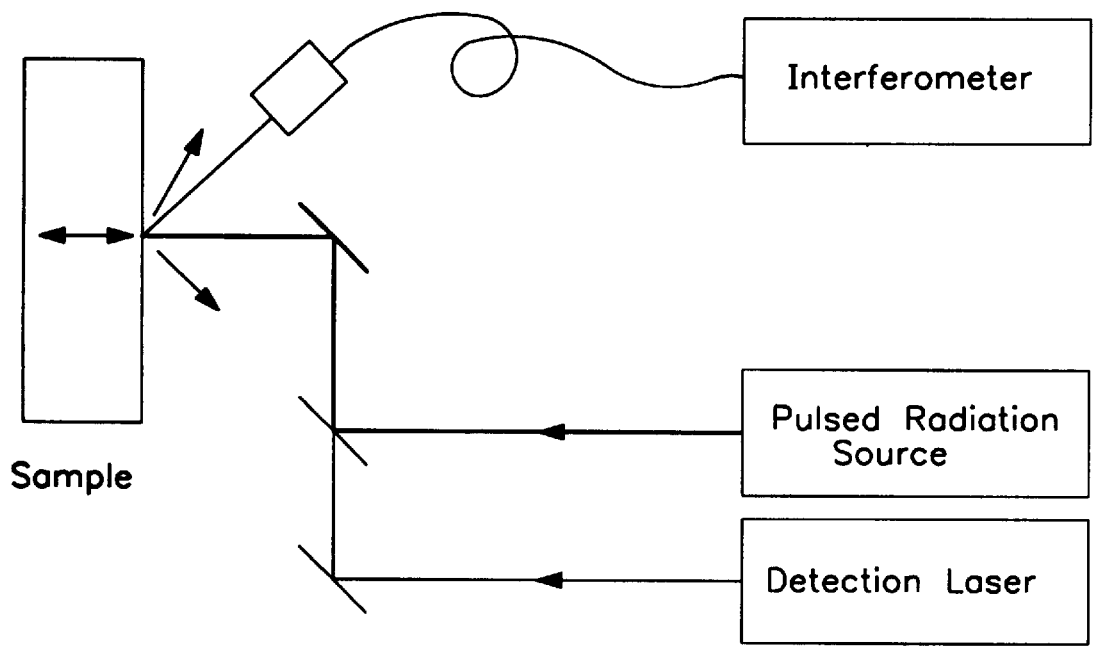
FIG. 10B is a schematic block diagram illustrating yet another alternate embodiment of the present invention.

Also, another alternate embodiment is shown in FIG. 10B, wherein the pulsed radiation source, the detection laser, and the interferometer are on the same side of the sample, as opposed to FIGS. 1, 9, and 10A where the detection laser and the interferometer are on the opposite side of the pulsed radiation source.

Furthermore, although the preferred embodiment has been described as selecting the 2L, $3S_s$, and $3S_f$ resonances, the present invention is not limited thereto, and any one or more other resonances may be selected.

In like fashion, although the preferred embodiment has been described using a confocal Fabry-Perot interferometer, the present invention is not limited thereto, and other type and variety of laser interferometers may be employed, such as a Michelson, Mach-Zender, photorefractive, photo-emf, or any other type of interferometer with a detection bandwidth that includes the frequencies of the resonance peaks of interest, and with good signal to noise characteristics.

Although spectroscopy may be effected by the present invention without moving the generation laser or laser interferometer (i.e., keeping them stationary), the generation laser and the laser interferometer, and the object may be moved relative to one another, so as to scan across a line (as in FIG. 8), or even across an area.

As has been described above, by means of the present embodiment, it is possible to effect laser detection of not only laser-generated longitudinal resonances, but also laser-generated shear resonances in an object, and therefrom to determine physical properties such as thickness which is corrected for texture, crystallographic orientation distribution measurements, and the like. Furthermore, it is possible to do so using a single pulse from the generation laser 200, which yields a single wideband ultrasonic pulse, without requiring circuitry for sweeping of a narrow band signal through a spectrum of frequencies to excite the various resonances. Other advantages include (1) the ability to dispose the apparatus at a large standoff distance (e.g., from several inches to several meters) from the object (in contrast to conventional non-laser ultrasonics which typically require close proximity, e.g., 1 mm, or a couplant such as water), and (2) the ability to dispose the generation laser at a wide range of angles without greatly affecting the generation of ultrasonic pulses. In contrast to conventional non-laser ultrasonics which typically exhibit angular dependence, the present invention is substantially orientation insensitive.

Except as otherwise disclosed herein, the various components shown in outline or in block form in the figures are individually well known and their internal construction and operation are not critical either to the making or using of this invention or to a description of the best mode of the invention.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. An apparatus comprising:

generating means for applying a radiation pulse from a pulsed source of radiation to an object to generate elastic waves therein;

detecting means for optically detecting the elastic waves generated in the object by said generating means, wherein said detecting means comprises an interferometer for optically detecting the elastic waves; and analyzing means for analyzing the elastic waves optically detected in the object by said detecting means, said analyzing means comprising shear resonance identifying means for identifying at least one shear resonance in the object in accordance with the elastic waves optically detected in the object by said detecting means, wherein the elastic waves are generated in the object without frequency sweeping, and wherein the radiation pulse generates a broadband ultrasonic pulse in the object, whereby said generating means simultaneously excites a broad frequency spectrum of elastic waves in the object.

2. An apparatus according to claim 1, wherein the pulsed source of radiation comprises a pulsed laser.

3. An apparatus according to claim 1, wherein said detecting means further comprises a laser.

4. An apparatus according to claim 1, wherein said interferometer comprises a confocal Fabry-Pérot interferometer.

5. An apparatus according to claim 1, wherein the elastic waves generated by said generating means propagate in a direction perpendicular to a surface of the object.

6. An apparatus according to claim 5, wherein the object is a polycrystalline aggregate having one of (i) an isotropic crystallographic orientation distribution and (ii) an anisotropic crystallographic orientation distribution.

7. An apparatus according to claim 1, wherein the object is a plate, and the at least one shear resonance propagates in a direction of the thickness of the plate.

8. An apparatus according to claim 7, wherein the plate is a polycrystalline aggregate having weak elastic anisotropy, the polycrystalline aggregate is made of cubic crystallites, and the plate has orthotropic elastic symmetry.

9. An apparatus according to claim 6, further comprising crystallographic orientation distribution determining means for determining a measurement of the crystallographic orientation distribution of the polycrystalline aggregate in accordance with a shear resonance identified by said shear resonance identifying means.

10. An apparatus according to claim 1, wherein said analyzing means further comprises frequency domain representation determining means for determining a representation of elastic wave amplitude as a function of frequency in accordance with the elastic waves optically detected in the object by said detecting means.

11. An apparatus according to claim 10, wherein said shear resonance identifying means comprises means for identifying a shear resonance in accordance with the representation determined by said frequency domain representation determining means.

12. An apparatus according to claim 10, wherein said shear resonance identifying means comprises shear resonance frequency determining means for determining the resonance frequency of a shear resonance in accordance with the representation determined by said frequency domain representation determining means.

13. An apparatus according to claim 12, wherein said shear resonance identifying means further comprises shear resonance order calculating means for calculating the order of a shear resonance by dividing the resonance frequency of the shear resonance determined by said shear resonance frequency determining means by an estimate of the resonance frequency of a fundamental shear resonance and taking the nearest integer.

14. An apparatus according to claim 13, wherein the estimate of the resonance frequency of a fundamental shear resonance is obtained as a function of (i) a shear wave velocity and (ii) the dimensions of the object.

15. An apparatus according to claim 14, wherein the estimate of the resonance frequency of a fundamental shear resonance is obtained by dividing a shear wave velocity by twice the thickness of the object.

16. An apparatus according to claim 13, wherein the estimate of the resonance frequency of a fundamental shear resonance is obtained by estimating the resonance frequency of the fundamental longitudinal resonance by calculating the inverse of a time delay between two successive echoes of longitudinal elastic waves in the object, and multiplying the estimated resonance frequency of the fundamental longitudinal resonance by a ratio of shear to longitudinal wave velocity.

17. An apparatus according to claim 13, wherein the estimate of the resonance frequency of a fundamental shear resonance is obtained by calculating a common divisor of resonance frequencies of plural shear resonances.

18. An apparatus according to claim 10, wherein said analyzing means further comprises digital sampling means for sampling output of said detecting means, and said frequency domain determining means comprises means for performing a discrete Fourier transform upon the output of said digital sampling means.

19. An apparatus according to claim 1, further comprising property determining means for determining at least one of (i) a geometrical property, (ii) a physical property, or (iii) a microstructural property of the object, in accordance with a shear resonance identified by said shear resonance identifying means.

20. An apparatus according to claim 1, wherein said interferometer comprises an interferometer selected from the group consisting of Michelson, Mach-Zender, photorefractive, and photo-emf interferometers.

21. An apparatus according to claim 1, wherein the radiation pulse is ablative.

22. A laser-ultrasonic spectroscopy device, comprising:

a laser for directing a laser pulse to an object to generate elastic waves in the object;

a laser-interferometer for detecting surface displacements in the object arising from the elastic waves generated by the laser pulse of said laser;

a converter for converting the surface displacements detected by said laser-interferometer from the time domain to the frequency domain to obtain frequency domain data;

a shear resonance detector for detecting and measuring at least one shear resonance in accordance with the frequency domain data; and a property calculator for calculating at least one of a geometrical property, a physical property, and a microstructural property of the object in accordance with the at least one shear resonance detected and measured by said shear resonance detector, wherein the elastic waves are generated in the object without frequency sweeping, and wherein the laser pluse generates a broadband ultrasonic pulse in the object, whereby said laser simultaneously excites a broad frequency spectrum of elastic waves in the object.

23. A device according to claim 22, wherein said shear resonance detector detects and measures a plurality of shear resonances in accordance with the frequency domain data, and said property calculator calculates the properties of the object in accordance with the plurality of shear resonances detected and measured by said shear resonance detector.

24. A device according to claim 22, wherein said property calculator calculates at least one of (i) a thickness of the object and (ii) a crystallographic orientation distribution coefficient of the object, in accordance with the at least one shear resonance detected and measured by said shear resonance detector.

25. A device according to claim 22, further comprising a longitudinal resonance detector for detecting and measuring a longitudinal resonance in accordance with the frequency domain data, wherein said property calculator calculates at least one of (i) thickness of the object and (ii) a crystallographic orientation distribution coefficient of the object, in accordance with the at least one shear resonance detected and measured by said shear resonance detector and the longitudinal resonance detected and measured by said longitudinal resonance detector.

26. A device according to claim 22, wherein the laser pulse is ablative.

27. A method for generating and optically detecting a shear resonance in an object, said method comprising:
   applying a radiation pulse from a pulsed source of radiation to an object to generate elastic waves therein;
   optically detecting, using an interferometer, the elastic waves generated in the object by said applying step; and
   analyzing the elastic waves optically detected in the object by said detecting step, said analyzing step comprising a shear resonance identifying step of identifying at least one shear resonance in the object in accordance with the elastic waves optically detected in the object by said detecting step,
   wherein the elastic waves are generated in the object without frequency sweeping, and
   wherein the radiation pulse generates a broadband ultrasonic pulse in the object, whereby said applying step simultaneously excites a broad frequency spectrum of elastic waves in the object.

28. A method according to claim 27, wherein said detecting step uses the interferometer and a laser to optically detect the elastic waves generated in the object.

29. A method according to claim 27, wherein the radiation pulse is ablative.

30. A method comprising:
   directing a laser pulse to an object to generate elastic waves in the object;
   optically detecting, using an interferometer, surface displacements in the object arising from the elastic waves generated by the laser pulse of the laser;
   converting the surface displacements detected by said detecting step from the time domain to the frequency domain to obtain frequency domain data;
   a shear resonance detecting step of detecting at least one shear resonance in accordance with the frequency domain data; and
   calculating properties of the object in accordance with the at least one shear resonance detected by said shear resonance detecting step,
   wherein the elastic waves are generated in the object without frequency sweeping, and
   wherein the laser pulse generates a broadband ultrasonic pulse in the object, whereby said directing step simultaneously excites a broad frequency spectrum of elastic waves in the object.

31. An apparatus according to claim 8, further comprising crystallographic orientation distribution determining means for determining a measurement of the crystallographic orientation distribution of the polycrystalline aggregate in accordance with a shear resonance identified by said shear resonance identifying means.

32. An apparatus according to claim 31, wherein said crystallographic orientation distribution determining means determines the $W_{420}$ crystallographic orientation distribution coefficient by using the following formula:

$$W_{420} = \frac{56\sqrt{5}\, \rho e^2 (f_{Sslow}^2 / n_{Sslow}^2 - f_{Sfast}^2 / n_{Sfast}^2)}{64\pi^2 A}$$

wherein e is the thickness of the plate, $f_{Sslow}$ is the resonance frequency of a slow shear resonance identified by said shear resonance identifying means, $n_{Sslow}$ is the order of the slow shear resonance, $f_{Sfast}$ is the resonance frequency of a fast shear resonance identified by said shear resonance identifying means, $n_{Sfast}$ is the order of the fast shear resonance, $\rho$ is the mass density of the plate, $\lambda$ and $\mu$ are the Lamé elastic constants of the plate in the isotropic approximation, and A is the anisotropy factor of the cubic crystallites.

33. An apparatus according to claim 19, wherein said property determining means determines a thickness of the object in accordance with a shear resonance identified by said shear resonance identifying means.

34. An apparatus according to claim 19, wherein said property determining means determines elastic constants of the object in accordance with a shear resonance identified by said shear resonance identifying means.

35. An apparatus according to claim 19, wherein said property determining means determines the plastic strain ratio of the object in accordance with a shear resonance identified by said shear resonance identifying means.

36. An apparatus according to claim 19, wherein said property determining means determines the crystallographic orientation distribution of the object in accordance with a shear resonance identified by said shear resonance identifying means.

37. A method according to claim 30, wherein said detecting step uses the interferometer and a laser to optically detect the elastic waves generated in the object.

38. A method according to claim 30, wherein the laser pulse is ablative.

39. An apparatus, comprising:
   a pulsed source of radiation for applying a radiation pulse to an object to generate elastic waves therein;
   an interferometer for optically detecting surface displacements in the object arising from the elastic waves generated by the radiation pulse generated by said pulsed source of radiation; and
   a resonance detector for detecting, in accordance with the surface displacements detected by said interferometer, a resonance of elastic waves propagating in the direction of the thickness of the object and having a polarization along an axis perpendicular to the direction of propagation,
   wherein the elastic wave generated in the object without frequency sweeping, and
   wherein the radiation pulse generates a broadband ultrasonic pulse in the object, whereby said pulsed source of radiation simultaneously excites a broad frequency spectrum of elastic waves in the object.

40. An apparatus according to claim 39, wherein said resonance detector detects a first resonance of elastic waves propagating in a direction of the thickness of the object and having a polarization along an axis perpendicular to the direction of propagation and a second resonance of elastic waves propagating in a direction of the thickness of the object and having a polarization along another axis perpendicular to the direction of propagation.

41. An apparatus according to claim 39, wherein said resonance detector further detects, in accordance with the surface displacements detected by said interferometer, a resonance of elastic waves propagating in the direction of the thickness of the object and having a polarization in the direction of propagation.

42. An apparatus according to claim 1, wherein said generating means and said detecting means are disposed on the same side of the object.

43. An apparatus according to claim 1, wherein said generating means and said detecting means are disposed on opposite sides of the object.

44. An apparatus according to claim 39, wherein a laser is used with said interferometer for optically detecting the surface displacements.

45. An apparatus according to claim 39, wherein the radiation pulse is ablative.

\* \* \* \* \*